(12) United States Patent
Wiedmann et al.

(10) Patent No.: US 11,389,124 B2
(45) Date of Patent: Jul. 19, 2022

(54) X-RAY PHASE CONTRAST DETECTOR

(71) Applicant: General Electric Company, Schenectady, NY (US)

(72) Inventors: Uwe Wiedmann, Clifton Park, NY (US); Biju Jacob, Niskayuna, NY (US); Peter Michael Edic, Albany, NY (US); Brian David Yanoff, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/789,100

(22) Filed: Feb. 12, 2020

(65) Prior Publication Data

US 2021/0244373 A1  Aug. 12, 2021

(51) Int. Cl.
| | | |
|---|---|---|
| *A61B 6/00* | (2006.01) | |
| *G01N 23/041* | (2018.01) | |
| *G01T 1/20* | (2006.01) | |
| *G01T 1/24* | (2006.01) | |

(52) U.S. Cl.
CPC ........... *A61B 6/4233* (2013.01); *A61B 6/484* (2013.01); *G01N 23/041* (2018.02); *G01T 1/20184* (2020.05); *G01T 1/241* (2013.01); *G01T 1/247* (2013.01); *G01N 2223/064* (2013.01); *G01N 2223/304* (2013.01); *G01N 2223/401* (2013.01)

(58) Field of Classification Search
None
See application file for complete search history.

(56) References Cited

U.S. PATENT DOCUMENTS

| | | | | |
|---|---|---|---|---|
| 4,303,860 | A * | 12/1981 | Bjorkholm | G01T 1/2018 250/363.02 |
| 4,937,453 | A * | 6/1990 | Nelson | G01T 1/2018 250/370.09 |
| 5,117,114 | A | 5/1992 | Street et al. | |
| 5,821,541 | A | 10/1998 | Tumer | |
| 7,399,972 | B2 * | 7/2008 | Yanada | G01T 1/2018 250/361 R |
| 8,017,906 | B2 * | 9/2011 | Nelson | G01T 1/2018 250/252.1 |
| 8,378,310 | B2 | 2/2013 | Bornefalk et al. | |

(Continued)

OTHER PUBLICATIONS

Beuville, E., et al.; High Resolution X-Ray Imaging Using a Silicon Strip Detector, IEEE Transactions on Nuclear Science, vol. 45, Issue 06, pp. 3056-3063.

(Continued)

*Primary Examiner* — Thomas R Artman (57) ABSTRACT

The present disclosure relates to fabrication and use of a phase-contrast imaging detector that includes sub-pixel resolution electrodes or photodiodes spaced to correspond to a phase-contrast interference pattern. A system using such a detector may employ fewer gratings than are typically used in a phase-contrast imaging system, with certain functionality typically provided by a detector-side analyzer grating being performed by sub-pixel resolution structures (e.g., electrodes or photodiodes) of the detector. Measurements acquired using the detector may be used to determine offset, amplitude, and phase of a phase-contrast interference pattern without multiple acquisitions at different phase steps.

15 Claims, 9 Drawing Sheets

(56) References Cited

U.S. PATENT DOCUMENTS

| | | | |
|---|---|---|---|
| 8,576,983 | B2 | 11/2013 | Baeumer et al. |
| 8,913,714 | B2 | 12/2014 | Michel et al. |
| 9,179,883 | B2 | 11/2015 | Spahn |
| 9,347,893 | B2* | 5/2016 | Nelson ............... G01N 23/041 |
| 9,402,594 | B2 | 8/2016 | Radicke |
| 10,162,066 | B2* | 12/2018 | Fu ....................... G01T 1/17 |
| 10,539,688 | B2* | 1/2020 | Steadman Booker ....................... G01T 1/2018 |
| 10,559,393 | B2* | 2/2020 | Proksa .................. A61B 6/484 |
| 10,605,916 | B2* | 3/2020 | Molnar ................. H04N 5/374 |
| 11,234,663 | B2* | 2/2022 | Proksa .................. A61B 6/484 |
| 2007/0007461 | A1* | 1/2007 | Yanada ................. G01T 1/2018 250/370.11 |
| 2009/0110144 | A1* | 4/2009 | Takahashi ............. G01T 1/241 378/62 |
| 2010/0246765 | A1 | 9/2010 | Murakoshi |
| 2010/0270462 | A1* | 10/2010 | Nelson .................. G01T 1/202 250/252.1 |
| 2013/0028379 | A1* | 1/2013 | Nelson ............. H01L 27/14601 378/62 |
| 2013/0235973 | A1 | 9/2013 | Murakoshi |
| 2015/0323679 | A1 | 11/2015 | Yang |
| 2018/0224564 | A1* | 8/2018 | Fu ......................... G01T 1/2928 |
| 2018/0226168 | A1* | 8/2018 | Proksa .................... G01T 7/00 |
| 2018/0328863 | A1 | 11/2018 | Rui et al. |
| 2019/0033448 | A1* | 1/2019 | Molnar ................. G01S 7/4814 |
| 2019/0219713 | A1* | 7/2019 | Steadman Booker .. G01T 1/208 |
| 2019/0304616 | A1 | 10/2019 | Koehler |
| 2019/0313991 | A1* | 10/2019 | Proksa .................. A61B 6/484 |
| 2020/0191967 | A1* | 6/2020 | Molnar ................. H04N 13/106 |

OTHER PUBLICATIONS

Prettyman, Thomas H., et al.; "Design and Characterization of Cylindrical CdZuTe Detectors with Coplanar Grids", SPIE 1999; Los Alamos National Laboratory LA-UR-99-3117; pp. 1-9.

Yoshida, Shoichi, et al.; "Application of Silicon Strip Detectors to X-Ray Computed Tomography", Nuclear Instruments and Methods in Physics Research Section, vol. 541, Issue 1-2, pp. 412-420, Feb. 2005.

Pfeiffer, Franz, et al.; "Phase Retrieval and Differential Phase-Contrast Imaging with Low-Brilliance X-Ray Sources", Nature Physics, vol. 2, pp. 258-261; Mar. 2006.

EP application 21154088.5 filed Jan. 28, 2021—Extended Search Report dated Sep. 27, 2021; 12 pages.

* cited by examiner

X-RAY PHASE CONTRAST DETECTOR

BACKGROUND

The subject matter disclosed herein relates to X-ray imaging and, in particular to phase-contrast imaging techniques.

Non-invasive imaging technologies allow images of the internal structures or features of a patient to be obtained without performing an invasive procedure on the patient. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient.

By way of example, in the context of X-ray absorption imaging techniques, X-rays are generated by an X-ray source and pass through an object or patient to reach a radiation detector. The X-rays are differentially absorbed as they pass through the object or patient based on the composition of the materials in the beam path. This differential X-ray absorption allows an image to be generated using the detected X-rays that provides information about internal structures of the object or patient. Such an image, which may be considered a conventional X-ray image, is useful for conveying information about materials that strongly absorb X-rays (i.e., high atomic weight or high-Z materials) such as bone, which exhibit high contrast with less absorptive materials. However, such X-ray absorption-based imaging approaches are less useful in generating information not related to the location of such high-Z materials. To address this deficiency, other imaging techniques may be employed. One such technique that also employs X-rays is phase-contrast imaging, which can yield information not available with conventional absorption X-ray imaging. In phase-contrast imaging, a series of gratings or a coherent source used in combination with fewer gratings can be employed to impart phase and interference properties to an X-ray beam. The resulting X-ray beam, when detected, yields additional information, particularly with respect to low atomic weight structures in the beam path as well as microstructures. One consequence of use of the gratings, however, is that a portion of the emitted X-rays may be absorbed by the gratings, which may necessitate higher X-ray doses to obtain suitable images.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a phase-contrast imaging detector is provided. In accordance with this embodiment, the phase-contrast imaging detector comprises a plurality of pixels. Each pixel comprises: a detection material that generates a measurable parameter in response to X-ray photons; and a plurality of sub-pixel resolution readout structures. The sub-pixel resolution readout structures are in an alternating pattern corresponding to a phase-contrast interference pattern. The phase-contrast imaging detector further comprises readout circuitry configured to read out signals from the plurality of sub-pixel resolution readout structures.

In a further embodiment, a phase-contrast imaging system is provided. In accordance with this embodiment, the phase-contrast imaging system comprises: an X-ray source configured to emit X-rays through an imaging volume during operation and at least one grating position in a path of X-rays through the imaging volume. The X-rays, upon passing though the at least one grating generate a spatial interference pattern. The phase-contrast imaging system further comprises a phase-sensitive detector configured to generate signals in response to X-rays emitted by the X-ray source and passing through the at least one grating. The phase-sensitive detector comprises a plurality of pixels. Some or all of the pixels each comprise a plurality of sub-pixel resolution readout structures. The sub-pixel resolution readout structures are in an alternating pattern corresponding to the phase-contrast interference pattern. The phase-contrast imaging system further comprises one or more processing components configured to process the signals generated by the plurality of sub-pixel resolution readout structures to generate clinical images.

In an additional embodiment, a method for phase-contrast imaging is provided. In accordance with this method, an X-ray source of an imaging system is operated to emit X-rays through an imaging volume. The X-rays are received at a phase-sensitive detector after the X-rays pass through at least one grating that imparts a spatial interference pattern to the X-rays. The phase-sensitive detector comprises a plurality of pixels. Some or all of the pixels each comprise a plurality of sub-pixel resolution readout structures. The sub-pixel resolution readout structures are in an alternating pattern corresponding to the phase-contrast interference pattern. Signals generated by the plurality of sub-pixel resolution readout structures are processed to determine an amplitude, an offset, and a phase of the phase-contrast interference pattern. A phase image, an absorption image, or a darkfield image are generated using at least one or more of the phase, the amplitude, and the offset.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

X-ray imaging is frequently used by medical practitioners to non-invasively acquire information about structures within the body of a patient. Conventional X-ray imaging relies on differential absorption of X-rays by structures of different composition within the body to provide useful data. In particular, such differentially absorbed X-rays may be used to generate images that exhibit good contrast for high atomic weight (i.e., high-Z) materials within the body, but provides limited information about features that do not readily absorb X-rays.

Phase-contrast imaging is also an X-ray based imaging technique, which often utilizes a series of gratings (e.g., absorption or phase gratings) to impart phase and spatial interference properties to the X-ray beam. The detected X-rays can then be used to reconstruct not only a conventional X-ray absorption image, but also a phase image (which has good contrast for low-Z materials, such as tissues) and a darkfield image (which allows sub-pixel microstructures, e.g., lung alveoli, to be detected though not resolved). In particular, a phase image may be useful in contexts where there are low-Z objects which a clinician wishes to view or detect in an environment that also includes high-Z features. One such example is a lesion within the liver parenchyma, where tissue properties between the liver and lesion vary slightly. To generate such phase images, the Compton absorption effect is measured without photoelectric absorption. However, the gratings employed in phase-contrast imaging to generate such images typically absorb a substantial portion of the X-rays emitted for imaging. As a result, higher X-ray doses are typically employed for phase-contrast imaging than for conventional absorption imaging.

The techniques disclosed herein help address these issues. In particular, as disclosed herein, certain implementations of the present invention eliminate one of the gratings (i.e., a detector-side grating, denoted as the analyzer grating) typically employed in phase-contrast imaging and employ a detector that integrates the function of this grating into the detector itself. In this manner loss of dose attributable to this grating is avoided. This is particularly important in medical imaging, where the X-rays absorbed by the detector-side grating would already have gone through the patient, thereby creating additional X-ray dose for the patient that does not reach the detector. In addition, incorporating this functionality into the detector also eliminates the need to take multiple acquisitions using an analyzer grating at different phase steps, as discussed in greater detail herein.

Figure 1:
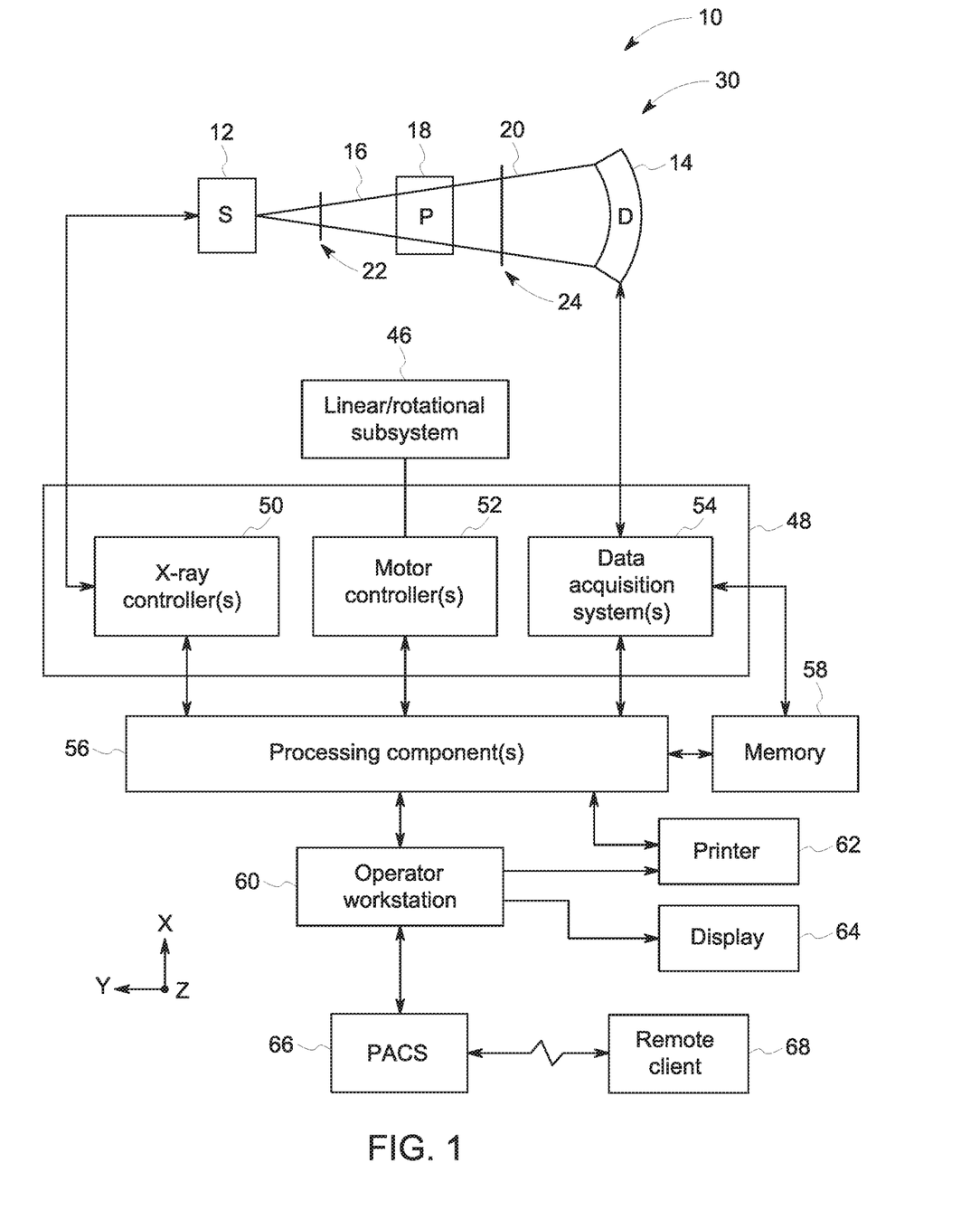
FIG. 1 is a diagrammatical view of an imaging system for use in producing images, in accordance with aspects of the present disclosure.

With the preceding in mind, an example of an X-ray imaging system 10 suitable for acquiring data for reconstruction as discussed herein is provided in FIG. 1. As may be appreciated, the X-ray based imaging system 10 may be any suitable X-ray imaging modality, such as a computed tomography (CT) imaging system, a C-arm type imaging system, a tomosynthesis imaging system, a conventional radiography imaging system, a mammography imaging system, a fluoroscopy imaging system, and so forth.

In the embodiment illustrated in FIG. 1, imaging system 10 includes a source of X-ray radiation 12 and a detector 14. The X-ray source 12 may be an X-ray tube or comprise one or more other sources of X-ray radiation suitable for the acquisition of medical or other images. The X-rays 16 generated by the source 12 pass into an imaging region in which an object to be imaged (e.g., a part undergoing non-destructive evaluation or testing), a tissue sample to be imaged, a bag or package undergoing security screening, a patient undergoing an imaging protocol, and so forth may be positioned. In the illustrated example, a patient 18 undergoing imaging is positioned within the imaging volume during a procedure. In the depicted example, the X-rays 16 are collimated to be a fan-shaped (planar) or cone-shaped (volumetric) beam, e.g., a fan-beam or cone-beam, which passes through the imaged volume.

A portion of the X-ray radiation 20 passes through or around the patient 18 (or other subject of interest) and impacts a detector array, represented generally as the detector 14. Detector elements (e.g., pixels) of the detector 14 produce electrical signals that represent the intensity of the incident X-rays 20 upon detector elements of detector 14. These signals are acquired and processed, as discussed herein, to reconstruct images of the features within the patient 18.

With respect to the detector 14 as used herein, various types of detectors are contemplated that may be suitable for phase-contrast imaging in accordance with the present invention. In general, a detector 14 as used herein will comprise an array of pixels. Each pixel is associated with some medium with which X-rays interact and with sub-pixel resolution electrodes that measure some property or signal generated in response to the interaction of the X-rays with the medium. In certain embodiments as discussed herein, the electrodes associated with a given pixel are in an interleaved or other discontinuous configuration (i.e. not a 1 dimensional or two dimensional array of contiguous electrodes) that in practice provides the ability to discriminate signal at sub-pixel resolutions within a given pixel, which may in certain implementations be leveraged to provide functionality comparable to what might be achieved by providing an analyzer grating at the surface of the detector 14.

In the context of a scintillator-based embodiment (e.g., in embodiments where a scintillator is used to convert high-energy X-ray photons to lower energy optical photons that are detected), the electrodes associated with each pixel may take the form of an interlaced or other discontinuous photodiode electrode structure suitable for reading out signals generated in response to the optical photons. In the context of a direct-conversion detector (i.e., a detector where there the X-ray photons are themselves detected and generate a responsive signal, such as via interaction with a semiconductor material, as opposed to a secondary photon generated by a scintillator), the electrodes associated with each pixel may similarly be provided as an interlaced or other non-continuous set of electrodes. Such direct-conversion type detectors may be configured to provide certain additional functionality, such as being energy-integrating and/or photon-counting type detectors. In photon-counting contexts, the coincidence detection and/or spectral information may also be acquired using the detector 14.

In the depicted example gratings 22, 24 (e.g., absorption or phase gratings) are positioned in the path of the X-ray beam. The grating 22 may be the only grating provided if the source 12 is sufficiently small and/or is coherent. In practice however, an additional source-side grating may be present near the source 12 to effectively cause a larger and/or incoherent source 12 to be perceived as a multitude of spatially-coherent line sources in a phase-contrast context. Such gratings may be present to facilitate phase-contrast imaging. In the depicted example an analyzer grating 24 opposite the patient 18 relative to the source 12 (i.e., on the detector-side) is also provided.

In the present example, the source 12 and detector 14 (as well as any gratings, filters, collimators, and so forth) may be a part of an imager subsystem 30. In certain imaging modalities (e.g., computed tomography (CT), C-arm angiography, tomosynthesis), the source 12 and detector 14 of the imager 30 may be moved relative to the patient or imaged object along one or more axes during a scan procedure for which projection data is acquired. For example, the imager 30 may move about a first axis of rotation, a second axis of rotation, or a third axis of rotation, or any combination thereof. In one embodiment, the translation and rotation of the imager 30 may be determined or coordinated in accordance with a specified protocol. Alternatively, the imager 30 may be held constant, while the object is repositioned, such as in non-destructive testing applications.

The movement of the imager 30, if any, may be initiated and/or controlled by one or more linear/rotational subsystems 46. The linear/rotational subsystems 46 may include support structures, motors, gears, bearings, and the like, that enable the relative rotational and/or translational movement of the imager 30. In one embodiment, the linear/rotational subsystems 46 may include a structural apparatus (e.g., a C-arm, rotating gantry, turntable, and so forth) supporting the source 12 and the detector 14 or, alternatively, the object or patient 18.

A system controller 48 may govern the linear/rotational subsystems 46 that initiate and/or control the movement of the components of the imager 30. In practice, the system controller 48 may incorporate one or more processing devices that include or communicate with tangible, non-transitory, machine readable media collectively storing instructions executable by the one or more processors to facilitate performance of imaging operations. The system controller 48 may also include features that control the timing of the activation of the source 12, for example, to control the acquisition of X-ray data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the imaging system 10 to execute examination protocols. It should be noted that, to facilitate discussion, reference is made below to the system controller 48 as being the unit that controls acquisitions, movements, and so forth, using the imager 30. However, embodiments where the system controller 48 acts in conjunction with other control devices (e.g., other control circuitry local to the imagers or remote to the system 10) are also encompassed by the present disclosure.

In the present context, the system controller 48 includes signal processing circuitry and various other circuitry that enables the system controller 48 to control the operation of the imager 30 and the linear/rotational subsystems 46. In the illustrated embodiment, the circuitry may include an X-ray controller 50 configured to operate the X-ray source 12. Circuitry of the system controller 48 may also include one or more motor controllers 52. The motor controllers 52 may control the activation of various components that are responsible for moving the source 12 and the detector 14. In other words, the motor controllers may implement a particular acquisition trajectory or motion for the relative motion of the components of the imager 30.

The system controller 48 is also illustrated as including one or more data acquisition systems 54. Generally, the detector 14 may be coupled to the system controller 48, and more particularly to the data acquisition systems 54. The data acquisition systems 54 may receive data collected by readout electronics of the detector 14 and in certain embodiments may process the data (e.g., by converting analog to digital signals or to perform other filtering, transformations, or similar operations).

It should be noted that the tangible, non-transitory, machine-readable media and the processors that are configured to perform the instructions stored on this media that are present in the system 10 may be shared between the various components of the system controller 48 or other components of the system 10. For instance, as illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform image acquisition and reconstruction techniques. Further, the processing components 56 and the memory components 58 may coordinate in order to perform various image reconstruction processes.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58.

The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of patient data, patient images, image acquisition parameters, and the like. This stored information may be shared throughout the imaging facility and may also be shared with other facilities, for example, a remote client 68. The remote client 68 may include hospitals, doctors' offices, or any other similar client.

Figure 2:
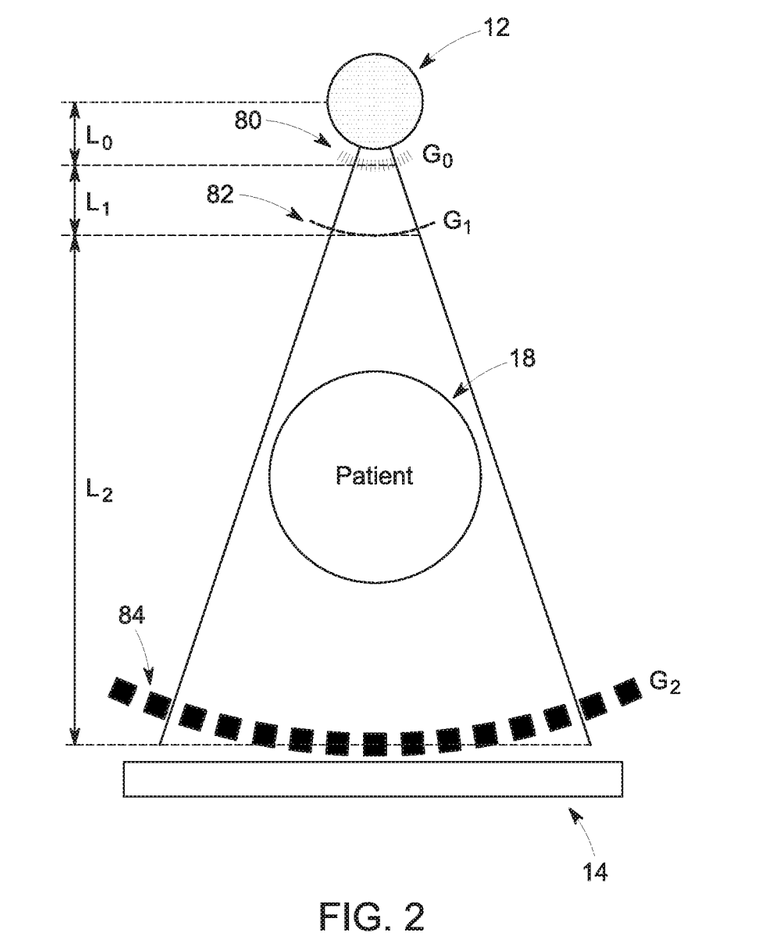
FIG. 2 depicts an example of a phase-contrast imaging system employing three gratings.

Various aspects of the present approaches may be further appreciated with respect to FIG. 2, which depicts features of a conventional phase-contrast imaging technique. Such phase-contrast imaging techniques typically determine a phase-shift angle for each voxel by comparing a spatial interference pattern observed with an object in the beam path with the spatial interference pattern when the object is absent. In the context of a conventional phase-contrast computed tomography (CT) imaging system, aspects of which are shown in FIG. 2, gratings (typically three gratings) may be employed to generate the interference patterns. In this example, a source-side grating $G_0$ (denoted by reference number 80) is positioned near X-ray source 12 to ensure spatial coherence and effectively creates an array of individually coherent, but mutually incoherent emissions in response to operation of an incoherent X-ray source. A phase object in the beam path causes a slight refraction for each coherent subset of X-rays. The angular deviation so introduced results in changes of the locally transmitted intensity through the pair of gratings $G_1$ and $G_2$ (denoted by reference numbers 82 and 84 respectively), which can be detected by an X-ray detector 14 (as shown in FIG. 1). In particular, grating $G_1$ 82 in such an arrangement is located between the source 12 and detector 14 and imprints a periodic interference pattern onto the wave front. The grating $G_2$ 84 is located proximate to the detector (i.e., $G_2$ is a detector-side grating) and resolves sub-pixel resolution interference pattern modulations. In practice, the gratings may be manufactured from silicon wafers using photolithography and electroplating where appropriate. It may be desirable for the $G_1$ grating 82 to be close to the source 12 so as to obtain the best sensitivity possible (which is a function of distance $L_2$ shown in FIG. 2).

Figure 3:
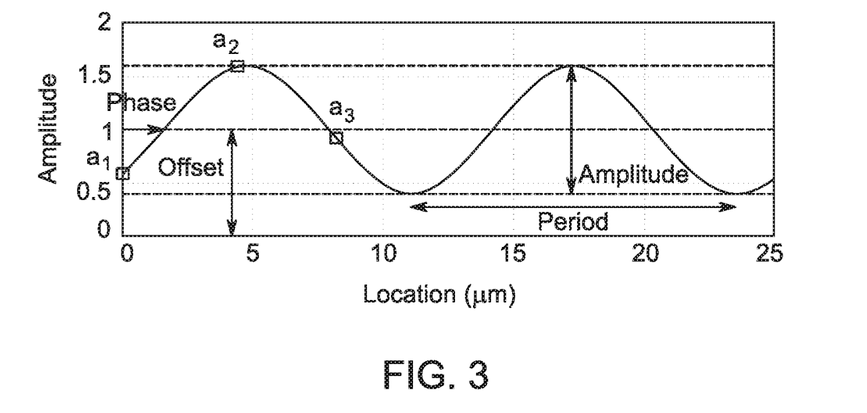
FIG. 3 depicts a generalized waveform illustrating parameters of a spatial interference pattern, in accordance with aspects of the present disclosure.

With respect to the spatial interference patterns created in phase-contrast imaging, and turning to FIG. 3, a brief explanation may be helpful in understanding the following discussion. In particular, the interference pattern created in phase-contrast imaging has three parameters that may be measured (period being known by design): (1) offset; (2) phase; and (3) amplitude. Offset as used herein results from the overall attenuation, as in conventional X-ray imaging. Phase is the spatial shift of the interference pattern relative to a reference, which corresponds to a gradient of the real part of the aggregate refractive index seen by an X-ray passing through an object under test. Amplitude of the interference pattern is the difference between the peaks and the valleys of the pattern, which may be reduced in the presence of microstructure. These three parameters are illustrated in FIG. 3 in the context of a sample pattern or waveform.

With the preceding in mind, while the conventional arrangement shown in FIG. 2 is suitable for phase-contrast imaging, such an arrangement may necessitate high X-ray flux since some portion of the X-rays are absorbed by each of the three gratings, reducing the flux that reaches the detector 14. By way of example, in contrast to conventional CT (i.e., absorption based imaging) where all of the X-ray flux reaches the detector 14 (absent that portion absorbed by the patient 18), in grating-based phase-contrast imaging only a limited portion (e.g., 25%) of the emitted flux may reach the detector 14 due to incidental absorption by the various gratings. In a medical context, this may result in higher flux being employed in order to freeze patient motion and obtain useful images. Grating $G_2$ 84 absorbs part of the X-ray flux that passes through the patient, thereby reducing dose efficiency of the imager subsystem 30.

Figure 4:
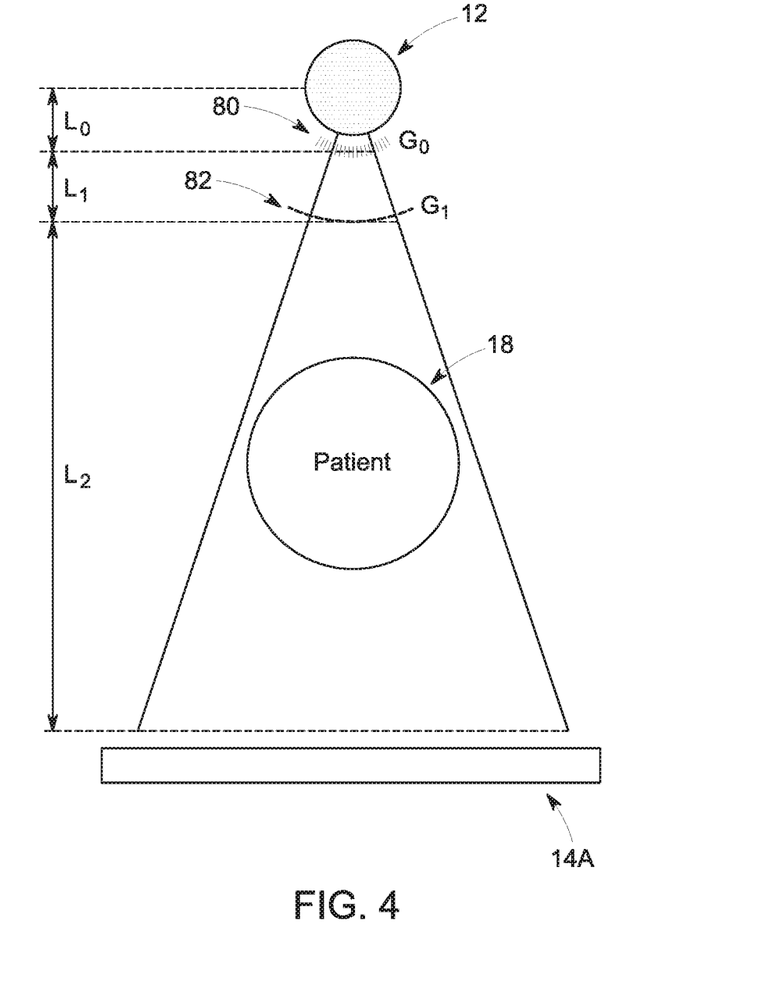
FIG. 4 depicts an example of a phase-contrast imaging system employing two gratings and a phase-sensitive detector, in accordance with aspects of the present disclosure.

To reduce the loss of flux attributable to the gratings in phase-contrast imaging, the present invention eliminates the detector-side grating $G_2$ 84 and integrates the functionality of this grating into a phase-sensitive detector 14A, as shown in FIG. 4. In addition to eliminating the loss of X-ray flux (and associated patient dose) due to X-ray absorption by grating $G_2$, this technique has the further benefit of eliminating the need to take multiple acquisitions at different phase steps, as is typical in a phase-contrast imaging protocol. In particular, in a conventional phase-contrast imaging acquisition, when an analyzer grating $G_2$ 84 is used in front of a standard CT detector, only a single measurement can be taken for each pixel at each time. For this reason, the analyzer grating $G_2$ 84, with apertures at a periodicity equaling the frequency of the interference pattern, is typically shifted, and additional (e.g., 3 total measurements) subsequent measurements are taken. By employing a phase-sensitive detector 14A (e.g., a detector in which multiple pixel electrodes provide sub-pixel resolutions corresponding to the period of the interference pattern, as discussed in greater detail below), all 3 independent measurements can be taken simultaneously.

Figure 5:
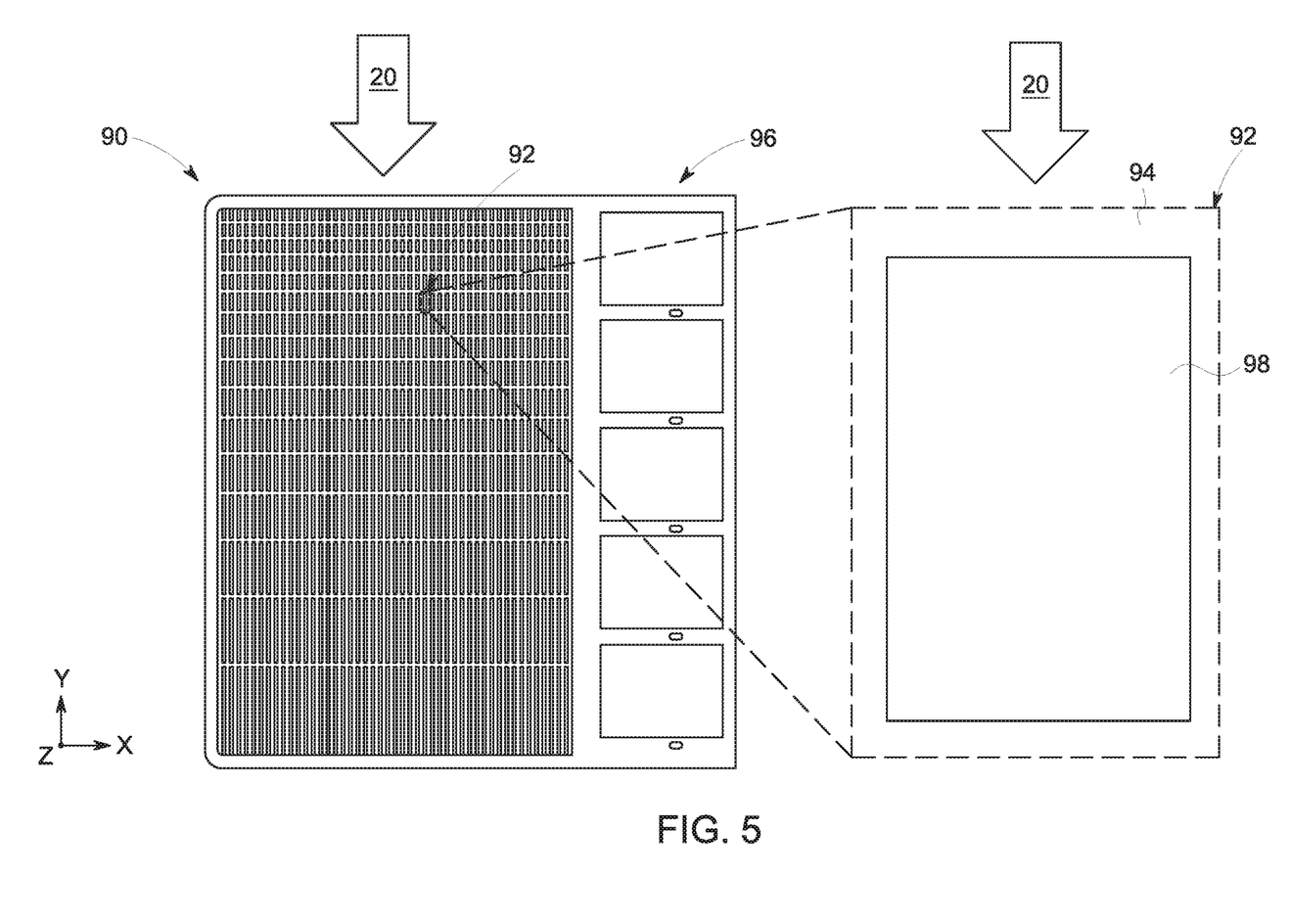
FIG. 5 depicts an example of a detector module and pixel.
Figure 6:
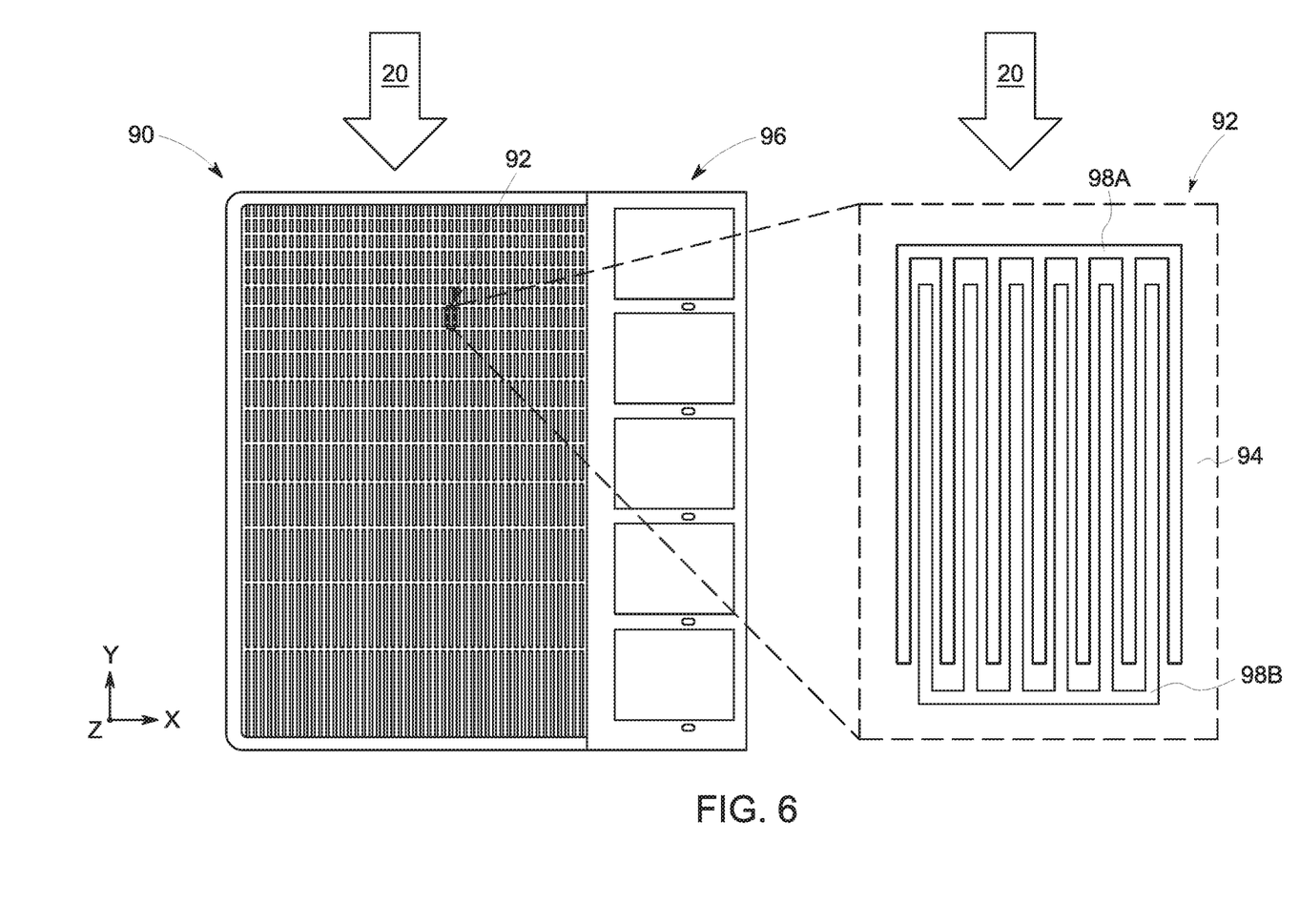
FIG. 6 depicts an example of a phase-sensitive detector module, in accordance with aspects of the present disclosure.
Figure 7:
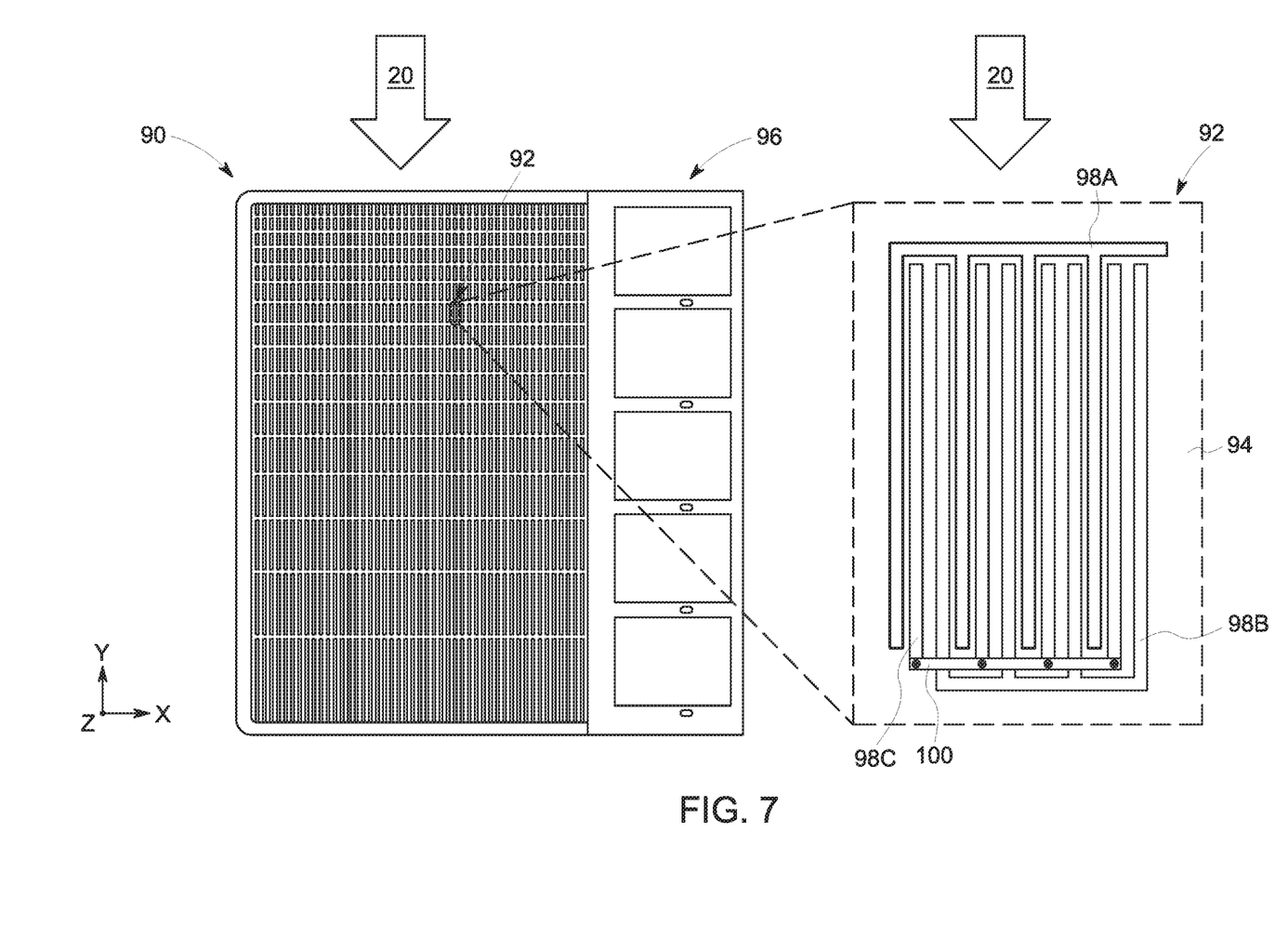
FIG. 7 depicts another example of a phase-sensitive detector module, in accordance with aspects of the present disclosure.

With this in mind, FIGS. 5, 6, and 7 depict examples of a detector module 90 that may be used to form a detector 14A and of pixels 92 provided in the detector module 90. In one embodiment, the detector module 90 comprises a plurality of pixels 92 formed using silicon, cadmium zinc telluride (CZT), cadmium telluride (CdTe), or other suitable detector materials that generate signal in response to X-rays without a scintillator intermediary component, i.e., direct-conversion detector materials. In other embodiments, however, a scintillator may be present as part of the detector 14, as discussed in greater detail with respect to FIGS. 8 and 9. As shown in FIGS. 5-7, the pixels 92 may increase in length in the direction of the X-ray beam path 20 so as to allow similar response at different depths within the detector. Alternatively, a single, long pixel may be provided that aligns with the direction of the X-ray beam. Readout circuitry 96 is depicted as being provided on the side or bottom of the detector module 90 so that detector modules 90 can be combined side-to-side or end-to-end to provide a large or configurable field-of-view.

With respect to these figures, FIG. 5 depicts a detection or conversion material 94 (such as a semiconductor material) associated with the pixel 92 with which X-rays interact. In the example of FIG. 5, within a respective pixel a single, continuous electrode 98 is associated with the conversion material 94 of the pixel 92. Conversely, FIGS. 6 and 7 depict that within a respective pixel 92, multiple, non-continuous electrodes 98A, 98B, and 98C are associated with the conversion material 94 of each respective pixel 92 to provide sub-pixel resolution measurements. In the depicted example, the electrodes of FIGS. 6 and 7 are provided as interlaced comb patterns, which may in one embodiment have sub-pixel resolution distances and separations corresponding to the frequency of the spatial interference pattern for a given phase-contrast imaging system.

For example, in FIG. 6 the electrodes 98A and 98B form a pattern of alternating arms comprising two interleaved combs. In FIG. 7 the electrodes 98A, 98B, and 98C form a pattern of alternating arms comprising three interleaved combs, one of which is spanned by a conductive bridge 100 provided outside the plane of the other conductive traces so as to allow separate electrical connection to each electrode. It may be noted that embodiments in which all pixels 92 of the detector module 90 have multiple, sub-pixel resolution electrodes are contemplated as well as embodiments in which only some of the pixels 92 of the detector module 90 have multiple, sub-pixel resolution electrodes, such as some or all of the pixels 92 in the center of the detector module 90. As discussed herein, the interlaced patterns of the electrodes 98 may have a spacing corresponding to the period of the phase-contrast interference pattern, thus allowing all three parameters of interest (i.e., offset, phase, and amplitude) to be measured simultaneously, as opposed to requiring multiple, discrete measurements in which an analyzer grating is shifted, requiring added acquisition time and patient dose. Although a pattern of two and three interleaved sub-pixel resolution electrodes are shown in FIGS. 6 and 7, respectively, alternate configurations using additional interleaved sub-pixel resolution electrodes as needed to accurately estimate the phase-contrast signals are contemplated.

The direction in which the electrodes 98 (or other patterned features, such as photodiodes) run may vary depending on the embodiment and may be either in the direction of the X-ray beam 20 (as shown) or orthogonal to the X-ray beam 20. When running parallel to the X-ray beam 20, the lines of the combs 98 form a line pattern in the direction of the X-ray beam 20, as shown in FIGS. 6 and 7. Conversely, when the pattern features are orthogonal to the X-ray beam 20, any pattern may be employed, including a coded aperture, that has spacing corresponding to the phase-contrast interference pattern, as noted above.

Figure 8:
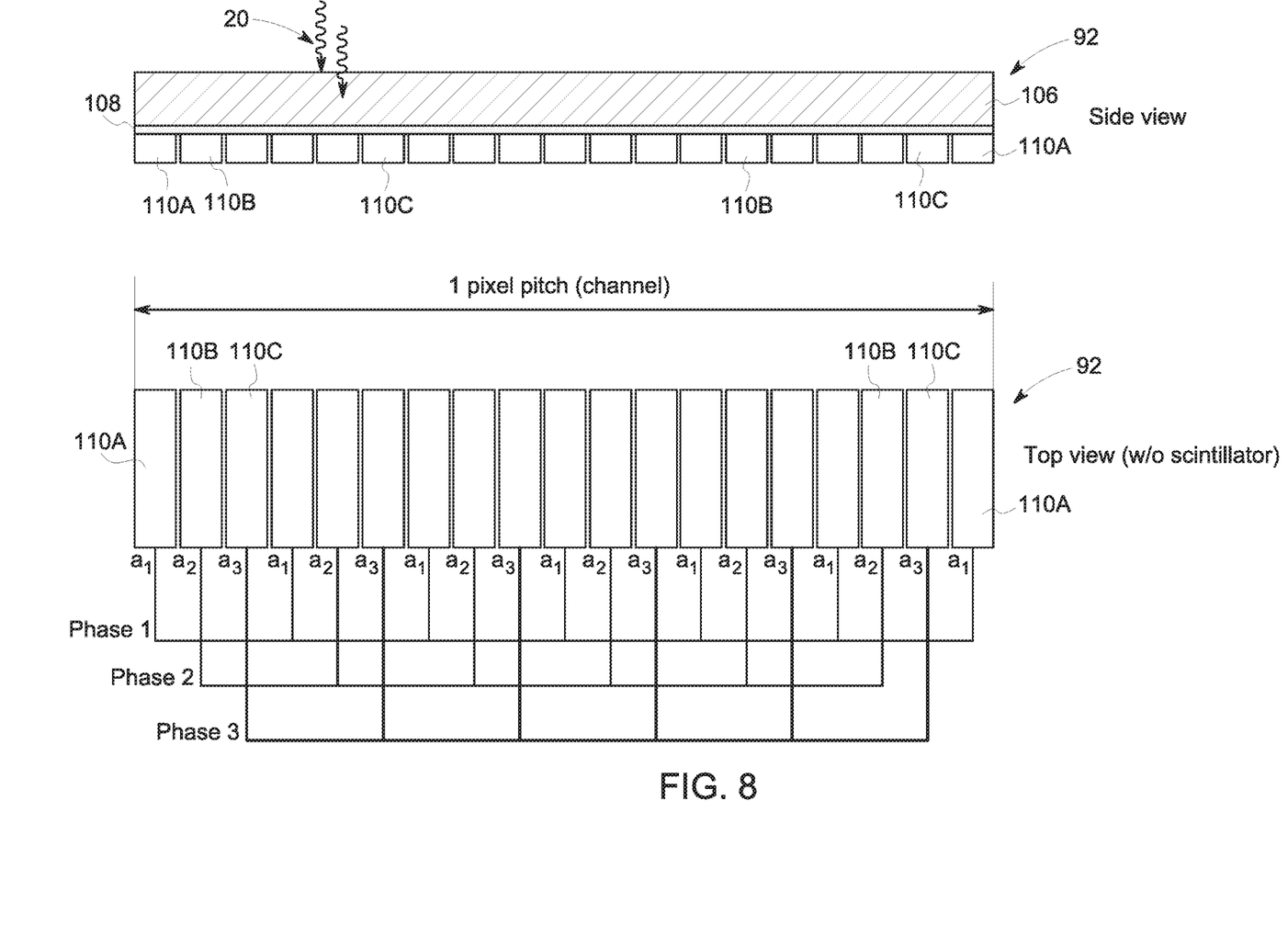
FIG. 8 depicts side and top views of a scintillator-based phase-sensitive detector pixel, in accordance with aspects of the present disclosure.

Turning to FIG. 8, another embodiment is illustrated which relates to a photodiode-based phase-contrast detector. In this example, a side-view (above) and a top-view (below) are illustrated together to better depict the various features. A single detector pixel 92 is illustrated, with the side-view illustrating the stack of components associated with the detector pixel 92 and the top-view illustrating only the sub-pixel photodiode arrangement with associated separate readout pathways ($a_1$, $a_2$, $a_3$) corresponding to the different phases 1, 2, and 3 of the spatial interference pattern.

In particular, the top-view shown in FIG. 8 depicts a high-resolution scintillator 106 in optical communication with multiple sub-pixel photodiodes 110 via an optical coupling layer 108, which may be absent in certain embodiments. The scintillator 106 may be formed from a high-Z material and may be arranged in columns or other structures corresponding to pixels 92 (i.e., the scintillator 106 may be pixelated) or may be monolithic with respect to the detector surface.

In the depicted example, X-ray photons 20 interact with the scintillator 106 to generate lower-energy photons (e.g., optical photons) that can be detected by the sub-pixel photodiodes 110. As shown, sub-pixel photodiodes 110 are grouped into an alternating, separated pattern to form three interleaved photodiodes 110A, 110B, and 110C have a separation distance corresponding to the frequency of the spatial interference pattern for the phase-contrast imaging system. In this example, the pixel 92 is read out using the three separate, interleaved sub-pixel photodiodes 110A, 100B, and 110C such that the readout channel associated with the pixel 92 is comprised of multiple sub-pixels. In certain implementations, the sub-pixel photodiodes 110 range in width from a few m (e.g., 2-5 µm) to several tens of m (e.g., 30-80 µm). In an embodiment, the sub-pixel photodiodes 110 may be manufactured as complementary metal-oxide semiconductor (CMOS) devices, lateral metal semiconductor metal (MSM) devices, and so forth. As in the preceding examples and by way of further illustration below, signals for corresponding (i.e., same phase) sub-pixel photodiodes 110 are combined to form the "phase" comb in either the pre-readout (i.e., the analog) domain or the post-readout (i.e., digital) domain. As above, although a pattern of three interleaved sub-pixel resolution electrodes are shown in FIG. 8, alternate configurations using 2 or more interleaved sub-pixel resolution photodiodes as needed to accurately estimate the phase-contrast signals are contemplated.

Figure 9:
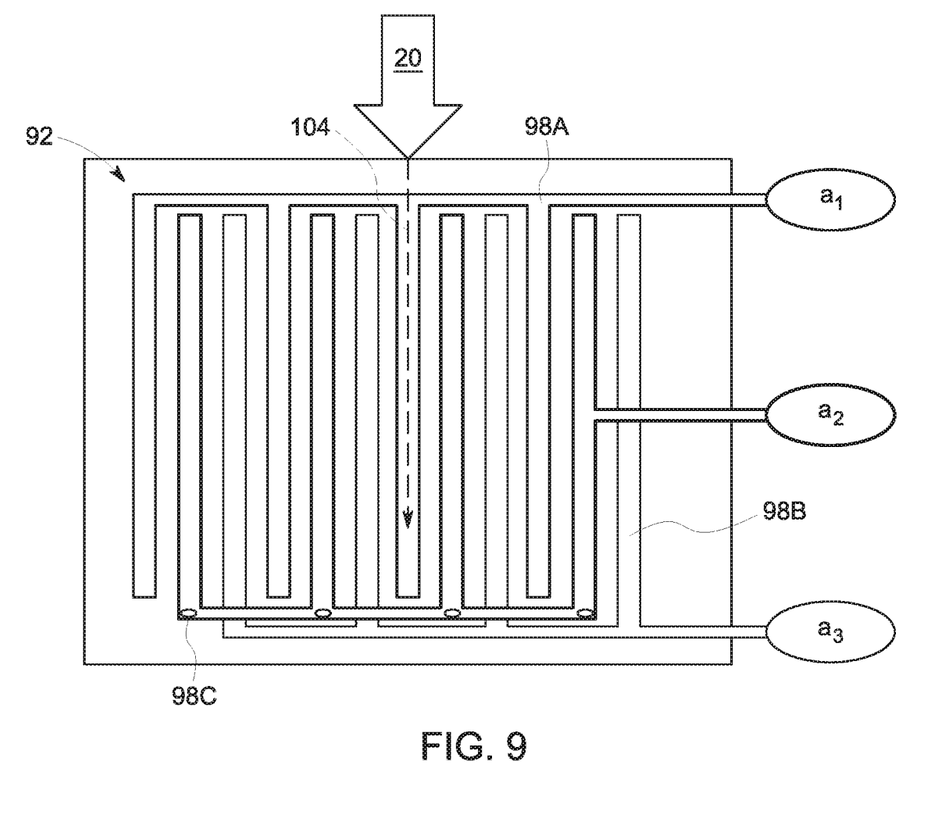
FIG. 9 depicts an example of a pixel comprising three interleaved comb structures, in accordance with aspects of the present disclosure.

Turning to FIG. 9, a patterned pixel having a pattern of three interleaved combs 98A, 98B, 98C as seen in FIG. 7 is illustrated in conjunction with an X-ray photon 104 that interacts with the detection material (e.g., direct-conversion material or, alternatively, scintillator material) to generate measured signals $a_1$, $a_2$, and $a_3$ that may be read out for the pixel 92. For each detected X-ray photon 104, a charge cloud is created that spreads out while traveling through the detection material or intermediary substrate to generate a signal that is measured or detected by one or more of the sub-pixel resolution electrodes 98 (or, alternatively, photodiodes 110). In this manner, the total energy deposited during the event (i.e., by a given X-ray photon interaction) can be determined. In detector systems equipped with coincidence detection logic (discussed in greater detail below), measurements at different electrodes 98 (or photodiodes 110 as appropriate) may be determined to be coincident in time and therefore attributed to the same X-ray photon. Further, the center of the charge cloud (i.e., position in the interference pattern) may be localized at sub-pixel resolution and the size of the charge cloud (which may depend on the depth within the detection material at which the photon is absorbed, as well as on the photon energy) can be determined with greater accuracy. With this in mind, the measurements $a_1$, $a_2$, and $a_3$ associated with the different respective electrodes 98 (or photodiodes 110) detecting an X-ray photon event can be used to determine the three parameters of interest for a single X-ray photon.

For example, and with reference to FIG. 3, one may assume the interference pattern has an intensity distribution I(x) in the form of:

$$I(x) = A_{DC} + \frac{A}{2}\sin\left(\frac{2\pi x}{p} - \varphi\right) \quad (1)$$

with period p, offset $A_{DC}$, amplitude A, and phase $\varphi$. Assuming this pattern is sampled in three locations that are each spaced one-third (⅓) of the period apart and with measured amplitudes $a_1$, $a_2$, and $a_3$, then $a_1$=I(0), $a_2$=I(p/3), and $a_3$=I(2p/3). As may be appreciated, it is not necessary to measure the period p as it is determined by the geometry of the system or setup. The parameters of the interference pattern can then be calculated from the measured amplitudes $a_1$, $a_2$, and $a_3$ in accordance with:

Offset ($A_{DC}$):

$$A_{DC} = \frac{a_1 + a_2 + a_3}{3} \qquad (2)$$

Amplitude (A):

$$A = 2\frac{\sqrt{2}}{3}\sqrt{(a_1 - a_2)^2 + (a_1 - a_3)^2 + (a_2 - a_3)^2} \qquad (3)$$

Phase (p):

$$\varphi = \sin^{-1} 2\frac{a_1 A_{DC}}{A} \text{ if } a_2 - a_3 \geq 0 \qquad (4)$$

$$\varphi = \pi - \sin^{-1} 2\frac{a_1 - A_{DC}}{A} \text{ if } a_2 - a_3 < 0$$

In this example, three sub-pixel measurement channels (i.e., $a_1$, $a_2$, $a_3$) are needed to unambiguously measure the three parameters of interest. Alternative formulas may be used to account for the size of the individual sub-pixel resolution electrodes or photodiodes, different numbers of sub-pixel resolution electrodes or photodiodes, to improve robustness in the presence of noise, and so forth. In certain embodiments, the detection threshold of the individual sub-pixel channels may be lowered relative to what would be used for a single pixel readout channel to avoid loss of signal, i.e., to take into account that the signal associated with an X-ray photon event may be split between multiple channels as opposed to being attributable to a single channel. That is, threshold-based cut-offs may be adjusted to take into account that a given signal may be split between two or more electrode readout channels, as opposed to a single electrode readout channel, to prevent discarding valid measurements. Coincidence detection logic may be employed to only count X-ray photon events where the sum of all channels is above a suitable, aggregate threshold value. That is, the detection threshold of the individual sub-pixel electrode channels may be lowered relative to a threshold that might be employed for a single electrode readout, while still requiring the sum of all sub-pixel channels to be at least equal to the threshold that would be employed if only a single electrode readout channel were employed.

Figure 10:
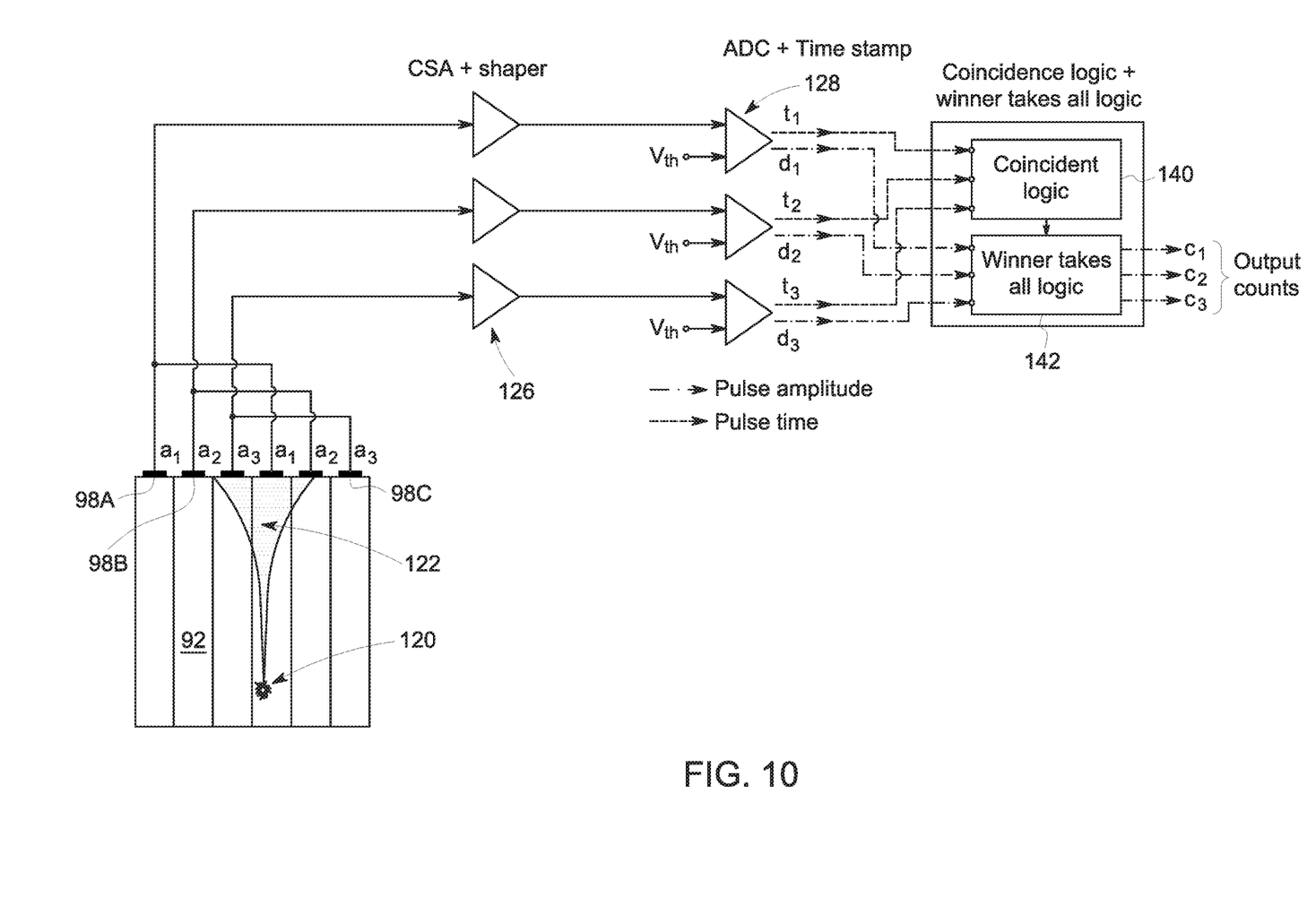
FIG. 10 depict an example of a coincidence logic implementation, in accordance with aspects of the present disclosure.

With respect to the charge cloud associated with an X-ray photon event and the use of the coincidence detection logic noted above, the significance of such logic in part pertains, as may be ascertained from the preceding discussion, to being able to assign or otherwise associate all of the detected charge for an X-ray photon event (which may be spread across multiple sub-pixel resolution electrodes 98 or photodiodes 110) to a single or primary sub-pixel resolution electrode 98 or photodiode 110. Turning to FIG. 10, one example of coincidence detection in the context of multiple sub-pixel resolution electrodes 98 (or photodiodes in an alternative context) is shown. In this example, an X-ray photon interacting with the detection material of a respective pixel 92 of a detector 14 (e.g., a photon-counting detector with built in analog-to-digital conversion ($A_{DC}$) per channel) causes an initial charge cloud 120 to be generated. A voltage applied between the top electrodes 98 and bottom electrode(s) (not shown) causes the charge cloud 120 to move and spread (denoted by reference number 122) toward the top electrodes (i.e., sub-pixel resolution electrodes 98), resulting in measurable signal ($a_1$, $a_2$, $a_3$) being generated at multiple electrodes 98. In this example, the signal (e.g., induced charge) at each electrode 98 is collected and processed by a respective charge sensitive amplifier (CSA) and shaper 126 per channel. The signal for each channel is passed to an $A_{DC}$ circuit 128 that is triggered by a comparator output based upon a threshold voltage, Vth, where Vth is set close to, but above the noise floor (e.g., 5 keV to 10 keV).

Each detected event generates a time stamp t and a digital output d for each relevant electrode (or photodiode). Time stamps t are passed to coincidence logic 140, which determines if a charge has been shared between electrodes 98 based on temporal proximity of the respective time stamps t. Based upon a determination that charge from an X-ray photon event was shared between electrodes 98, "winner-takes-all" logic may be activated and the correct (i.e., incident) counter is incremented for the electrode (or photodiode) determined to correspond to the location of the X-ray photon event (such as based on the largest measured signal). In certain implementations, the "winner-takes-all" logic may also require that the total energy measured for an X-ray event is greater than an energy threshold in order to increment the appropriate counter. In certain embodiments, a further "winner-takes-all" aggregation step may occur to account for potential charge sharing between pixels 92 (such as due to an X-ray photon being incident near the edges of two or more pixels 92).

Technical effects of the invention include a phase-contrast imaging detector having a detector that includes patterned pixel surfaces (e.g., interlaced or interleaved photodiodes or electrodes). A system using such a detector may employ only two gratings instead of three gratings to perform phase-contrast imaging, with the functionality of the third grating being performed by the discontinuous pattern of the pixel electrode or photodiode. Measurements acquired using the detector may be used to determine offset, amplitude, and phase of a phase-contrast interference pattern without multiple acquisitions at different phase steps of an analyzer grating.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A phase-contrast imaging detector, comprising:
a plurality of pixel elements, each pixel element comprising:
a detection material that generates a measurable parameter in response to X-ray photons;
a plurality of electrodes coupled to and interacting with the detection material, wherein the plurality of electrodes are in an alternating pattern of interleaved comb members with a spacing therebetween corresponding to a frequency of a phase-contrast interference pattern; and readout circuitry coupled to the plurality of electrodes and configured to read out signals from the plurality of electrodes;

wherein the alternating pattern of interleaved comb members of the plurality of electrodes are aligned in the same direction as an X-ray radiation beam emitted from an X-ray source;

wherein a path of the X-ray radiation beam is incident on multiple pixel elements aligned in the direction of the X-ray radiation beam; and wherein the pixel elements change in length in the direction of the path of X-ray radiation beam.

2. The phase-contrast imaging detector of claim 1, wherein the detection material comprises a direct-conversion material capable of generating a charge cloud in response to each X-ray photon, wherein the charge cloud is measured by the plurality of electrodes.

3. The phase-contrast imaging detector of claim 1, wherein the plurality of electrodes function as a detector-side analyzer grating in a phase-contrast imaging system.

4. The phase-contrast imaging detector of claim 1, wherein signals acquired from the plurality of electrodes are usable to simultaneously determine an amplitude, an offset, and a phase of the phase-contrast interference pattern without multiple acquisitions at different phase steps of an analyzer grating.

5. The phase-contrast imaging detector of claim 1, wherein the readout circuitry is configured to localize a center of a charge cloud to a respective electrode using coincidence logic, wherein the charge cloud is generated in response to an incident X-ray photon.

6. The phase-contrast imaging detector of claim 1, wherein the read out signals from the plurality of electrodes are used to simultaneously determine an offset, amplitude, and a phase of the phase-contrast interference pattern.

7. The phase-contrast imaging detector of claim 6, wherein an intensity distribution I(x) of the phase-contrast interference pattern is given as:

$$I(x) = A_{DC} + \frac{A}{2}\sin\left(\frac{2\pi x}{p} - \varphi\right)$$

with period p, offset $A_{DC}$, amplitude A, and phase $\varphi$.

8. A phase-contrast imaging system, comprising:
an X-ray source configured to emit X-rays through an imaging volume during operation;
at least one grating structure in a path of X-rays through the imaging volume, wherein the X-rays, upon passing though the at least one grating structure have a phase-contrast interference pattern;
a phase-sensitive detector configured to generate signals in response to X-rays emitted by the X-ray source and passing through the at least one grating structure, wherein the phase-sensitive detector comprises:
  a plurality of pixel elements, wherein some or all of the pixel elements each comprise a plurality of electrodes, wherein the plurality of electrodes are in an alternating pattern of interleaved comb members with a spacing therebetween corresponding to a frequency of the phase-contrast interference pattern; and
  one or more processing components configured to process the signals generated by the plurality of electrodes to generate images;
wherein the alternating pattern of interleaved comb members of the plurality of electrodes are aligned in the same direction as the X-rays emitted from the X-ray source;
wherein a path of the X-ray radiation beam is incident on multiple pixel elements aligned in the direction of the X-ray radiation beam; and
wherein the pixel elements change in length in the direction of the path of X-ray radiation beam.

9. The phase-contrast imaging system of claim 8, wherein the pixel elements further comprise a direct-conversion material capable of generating a charge cloud in response to each X-ray photon, wherein the charge cloud is measured by the plurality of electrodes.

10. The phase-contrast imaging system of claim 8, wherein the images comprise one or more of a phase image, an absorption image, or a darkfield image.

11. A phase-contrast imaging method comprising:
operating an X-ray source of an imaging system to emit X-rays through an imaging volume;
receiving the X-rays at a phase-sensitive detector after the X-rays pass through at least one grating structure that imparts a phase-contrast interference pattern to the X-rays, wherein the phase-sensitive detector comprises a plurality of pixel elements, wherein some or all of the pixel elements each comprise a plurality electrodes, wherein the plurality of electrodes are in an alternating pattern of interleaved comb members with a spacing therebetween corresponding to a frequency of the phase-contrast interference pattern;
processing signals generated by the plurality of electrodes to simultaneously determine an amplitude, an offset, and a phase of the phase-contrast interference pattern; and
generating a phase image, an absorption image, or a darkfield image using at least one of the phase, the amplitude, and the offset;
wherein the alternating pattern of interleaved comb members of the plurality of electrodes are aligned in the same direction as the X-rays emitted from the X-ray source;
wherein a path of the X-ray radiation beam is incident on multiple pixel elements aligned in the direction of the X-ray radiation beam; and
wherein the pixel elements change in length in the direction of the path of X-ray radiation beam.

12. The phase-contrast imaging method of claim 11, wherein the phase, the amplitude, and the offset are determined without multiple acquisitions at different phase steps of an analyzer grating.

13. The phase-contrast imaging method of claim 11, further comprising processing the signals generated by the plurality of electrodes to localize an incident X-ray photon.

14. The phase-contrast imaging method of claim 11, wherein the signals comprise measured voltages, and processing the signals comprises:
comparing each signal to a threshold voltage;
generating a time stamp and digital output for those signals exceeding the threshold voltage;
using the time stamps, identifying occurrences where signals generated in response to a respective X-ray photon were measured at more than one of the electrodes;

for occurrences where signals generated in response to the respective X-ray photon were measured at more than one of the electrodes, determining a location of the respective X-ray photon from respective signals from the more than one electrodes; and incrementing a counter associated with the respective electrode.

15. The phase-contrast imaging method of claim 14, wherein processing the signals further comprises:

shaping and amplifying a signal generated from at least one of a generated charge cloud and one or more lower-energy photons in response to each incident X-ray photon prior to comparing each signal to the threshold voltage.

\* \* \* \* \*